(12) United States Patent
Garson et al.

(10) Patent No.: US 11,369,745 B2
(45) Date of Patent: Jun. 28, 2022

(54) INJECTION DEVICE END OF DOSE INDICATOR

(71) Applicant: OWEN MUMFORD LTD, Oxfordshire (GB)

(72) Inventors: Daniel Garson, Oxfordshire (GB); Andreas Artelsmair, Oxfordshire (GB)

(73) Assignee: Owen Mumford Limited, Oxfordshire (GB)

( * ) Notice: Subject to any disclaimer, the term of this patent is extended or adjusted under 35 U.S.C. 154(b) by 273 days.

(21) Appl. No.: 16/586,469

(22) Filed: Sep. 27, 2019

(65) Prior Publication Data
US 2020/0101230 A1  Apr. 2, 2020

(30) Foreign Application Priority Data
Sep. 28, 2018 (GB) ..................................... 1815865

(51) Int. Cl.
*A61M 5/315* (2006.01)
*A61M 5/20* (2006.01)
*A61M 5/32* (2006.01)

(52) U.S. Cl.
CPC ........ *A61M 5/3157* (2013.01); *A61M 5/2033* (2013.01); *A61M 5/3202* (2013.01);
(Continued)

(58) Field of Classification Search
CPC .............. A61M 5/2033; A61M 5/3157; A61M 2005/2073; A61M 2205/581
(Continued)

(56) References Cited

U.S. PATENT DOCUMENTS

2013/0310744 A1* 11/2013 Brereton ............... A61M 5/326
604/196
2014/0243757 A1  8/2014 Dasbach et al.
(Continued)

FOREIGN PATENT DOCUMENTS

CN       102083489 A    6/2011
CN       103476445 A    12/2013
(Continued)

OTHER PUBLICATIONS

GB Search and Examination Report, dated Mar. 25, 2019, from corresponding GB application No. GB1815865.9.
(Continued)

*Primary Examiner* — Theodore J Stigell
*Assistant Examiner* — Nidah Hussain
(74) *Attorney, Agent, or Firm* — Quarles & Brady LLP (57) ABSTRACT

Disclosed is an injection device including a body for receiving a syringe, a firing mechanism including a reaction component, a plunger configured to be axially displaced in a forward direction relative to the reaction component, and a drive spring located between the reaction component and the plunger for driving the plunger forwards upon activation of the injection device, wherein the reaction component provides a reaction surface for the drive spring. The device further includes a locking mechanism for locking the reaction component in a first axial position within the body, the locking mechanism being configured to release the reaction component upon a predefined forward movement of the plunger thereby allowing the reaction component to be driven in a rearward axial direction by the drive spring until it impacts against the body or a component secured to the body to thereby emit an audible indication of an end of dose.

19 Claims, 5 Drawing Sheets

(52) U.S. Cl.
CPC .............. *A61M 2005/2026* (2013.01); *A61M 2005/2073* (2013.01); *A61M 2005/2086* (2013.01); *A61M 2205/581* (2013.01)

(58) Field of Classification Search
USPC ........................................................ 604/228
See application file for complete search history.

(56) References Cited

U.S. PATENT DOCUMENTS

| | | |
|---|---|---|
| 2017/0232201 A1 | 8/2017 | Holland et al. |
| 2017/0304541 A1 | 10/2017 | Bauss et al. |
| 2018/0147360 A1* | 5/2018 | Kemp ................. A61M 5/3157 |

FOREIGN PATENT DOCUMENTS

| | | |
|---|---|---|
| CN | 107073222 A | 8/2017 |
| EP | 2 698 179 A1 | 2/2014 |
| EP | 3 023 114 A1 | 5/2016 |
| JP | 5797209 B2 | 10/2015 |
| WO | 2015074977 A2 | 5/2015 |
| WO | 2017/032586 A1 | 3/2017 |

OTHER PUBLICATIONS

First Office Action from corresponding Chinese Patent Application No. 201910922458.5 dated May 8, 2021 (15 pages) (English translation included).

Extended European Search Report issued in European Patent Application No. 19198490.5 dated Dec. 13, 2019.

\* cited by examiner

INJECTION DEVICE END OF DOSE INDICATOR

CROSS-REFERENCE TO RELATED APPLICATIONS

The present application relates to and claims priority benefits from British Patent Application Serial No. GB 1815865.9, filed on Sep. 28, 2018, and entitled, "INJECTION DEVICE END OF DOSE INDICATOR," the contents of which are incorporated herein by reference in their entirety.

TECHNICAL FIELD

The invention relates to injection devices for delivering a fluid substance to a user or patient via a syringe and in particular to such devices having an end of dose indicator. In specific arrangements, the invention relates to auto-injectors for delivering the fluid under a force applied by a drive system.

BACKGROUND

Injection devices are used for the convenient administration of medicaments to patients. For example, injection devices, which may be auto-injectors, may be used for providing a single metered dose of a medicament. Such devices may be either single use "disposable" devices in which the device is typically provided with a syringe already installed, and which is not user-replaceable, or "reusable" devices which allow the user to replace the syringe when the medicament has been used.

It is noted that whilst the term "syringe" is used herein for clarity and consistency, this term is not intended to be limiting. In some arrangements the syringe may for example be a cartridge (which, for example, may be arranged to receive a disposable needle) or other medicament container. In some arrangements the syringe/cartridge/medicament container may be formed integrally with the (or part of the) injection device.

Injection devices may be provided in the form of an auto-injector device, in which delivery of the medicament is automated and the device may also be arranged to automate the insertion of a needle into the skin prior to the delivery of the medicament. However, it is noted that the term auto-injector may encompass injection devices that automatically insert the needle and devices which require the user to manually insert the needle.

Injection devices generally comprise a firing mechanism that is arranged to deliver a fluid from the syringe automatically under the force of a drive system, such as a drive spring. Optionally, injection devices may also comprise an insertion mechanism to displace the syringe within a housing of the injection device to cause needle penetration. The delivery arrangement generally acts via a plunger which includes a plunger and may also include or engage a piston (also referred to as a "bung") which is slidably provided within the syringe.

Injection devices may be designed and manufactured to accommodate different syringes. This provides a device that may be adapted to carry and operate syringes with different features and/or characteristics, such as different fill volumes. It is desirable to improve the safety and operability of such devices.

SUMMARY

Injection devices of the autoinjector type do not necessarily provide a tactile indication to users when a dose has been completely delivered such as the user will experience when using a manual device. As such it is desirable to incorporate into injection devices of the autoinjector type a means for providing an end of dose indication.

Methods and apparatus disclosed herein may be arranged to mitigate or solve one or more problems associated with the art, including those mentioned above and/or elsewhere herein.

According to a first aspect of the present invention there is provided an injection device comprising a body for receiving a syringe, a firing mechanism comprising a reaction component, a plunger configured to be axially displaced in a forward direction relative to the reaction component, and a drive spring located between the reaction component and the plunger for driving the plunger forwards upon activation of the injection device, wherein said reaction component provides a reaction surface for the drive spring. The device further comprises a locking mechanism for locking the reaction component in a first axial position within the body, the locking mechanism being configured to release the reaction component upon a predefined forward movement of the plunger thereby allowing the reaction component to be driven in a rearward axial direction by the drive spring until it impacts against said body or a component secured to the body to thereby emit an audible indication of an end of dose.

The locking mechanism may comprise a stop feature having a fixed axial position relate to said body, and a feature for causing a rotation of the reaction component within the body, substantially upon said predefined forward movement of the plunger, to move the reaction component out of a blocking engagement with said stop feature and thereby allow rearward movement of the reaction component.

The device may comprise a rear cap fixed to a rear end of said body, the rear cap providing said component against which the reaction component impacts to emit an audible indication of an end of dose, wherein the feature for causing a rotation of the reaction component within the body comprises a clutch has a substantially fixed axial position, the clutch being rotatable within the body by axial movement of the plunger towards the end of a delivery stroke to thereby cause said rotation of the reaction component. The clutch may be a substantially cylindrical component within which said plunger, said delivery spring and said reaction component and are coaxially accommodated. The reaction component may comprise an elongate rod extending through the delivery spring and an enlarged head at a rearward end of the rod, wherein the head provides said reaction surface and a surface that impacts the rear cap.

The end cap may comprise a skirt extending into the body from said rear end of the body and which defines a substantially longitudinally extending channel, said plunger and said reaction component being received within the skirt and being provided respectively with a plunger lug and a reaction component lug, said lugs being receivable within said channel to guide axial movement of the plunger and the reaction component.

The skirt may further defining a recess extending from said channel in a substantially circumferential direction and within which said lugs are located prior to device activation, said clutch being rotatable within the body upon activation to move the lugs into the channel.

The device may comprise a circumferential deviation of said channel rearwards of said recess in order to provide said stop feature, whereby the reaction component is prevented from moving rearward upon said activation but is permitted to move rearwards at the end of the plunger stroke.

The device may comprise a lockout shroud extending from a forward end of said body and being configured to cause activation of the device when pressed into the body, wherein said lockout shroud causes activation of the device by rotating said clutch as the lockout shroud is pressed into the body to thereby move the lugs of the plunger and the reaction component out of said recess and into the channel.

The drive spring may be a compression spring configured to expand upon activation of the device.

BRIEF DESCRIPTION OF THE DRAWINGS

Exemplary embodiments will be described herein with reference to the accompanying drawings, in which.

DETAILED DESCRIPTION

In the following embodiments, the terms "forward" and "front" refer to the patient facing end of the injection device or component thereof. In other words, the front end of the injection device is the end proximal to the injection site during use. Likewise, the term "rear" refers to the non-patient end of the injection device assembly or component thereof. In other words, the term "rear" means distant or remote from the injection site during use.

Many features of the exemplary arrangements disclosed herein are described as being "coupled" to other features. This term encompasses any coupling that results in the coupled features moving together in any direction, whether that be on a 1:1 basis or on some geared basis. The term "coupled" also encompasses any one of a connection between features, an abutment of one feature against another and an engagement of one feature with another, and such coupling may be direct or may be indirect, i.e. with a third feature therebetween.

Figure 1:
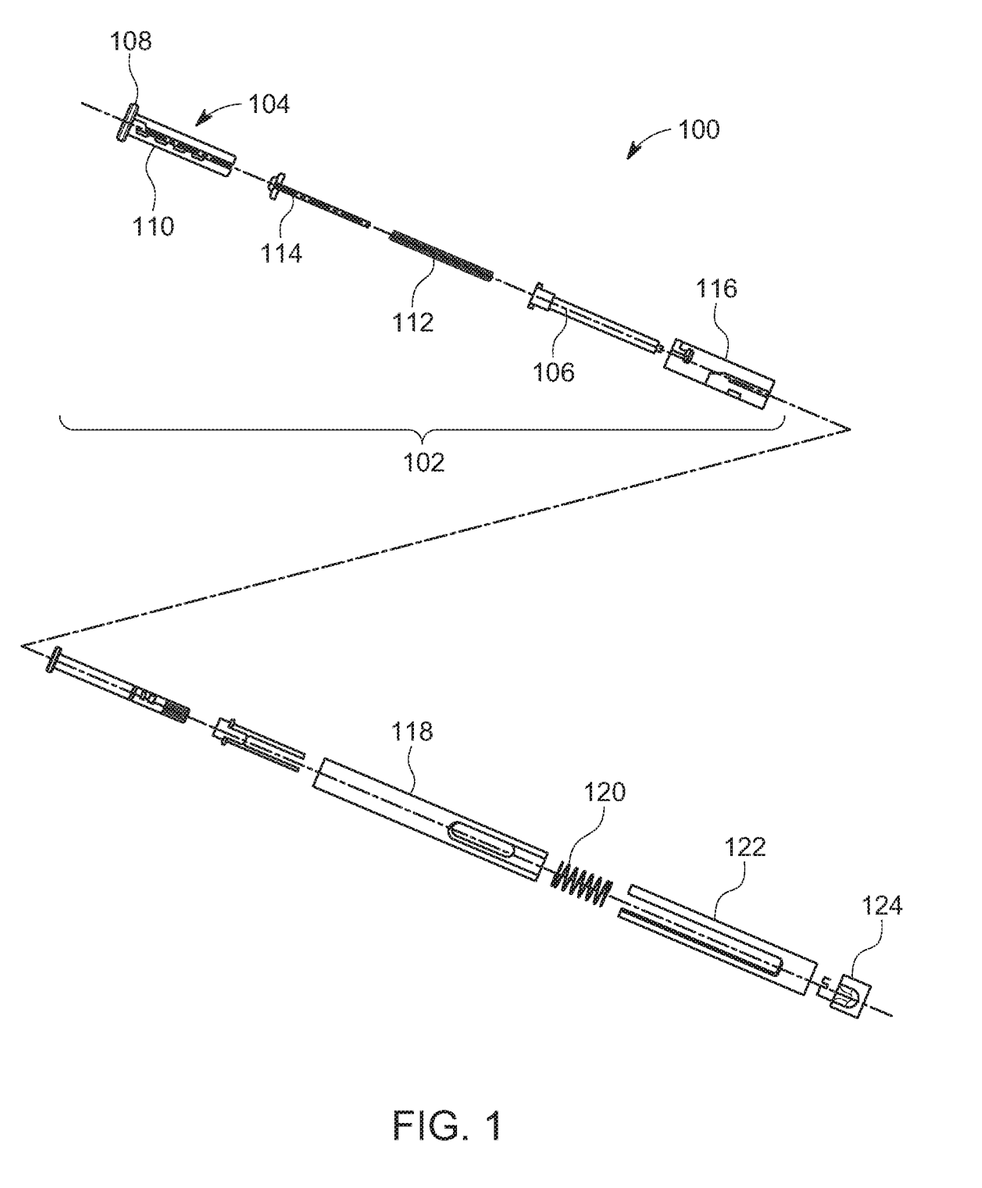
FIG. 1 is an exploded view of an auto-injector.

FIG. 1 shows an exploded view of an auto-injector 100. The auto-injector 100 comprises a firing assembly 102. The firing assembly comprises a rear cap 104 and a plunger 106. The rear cap 104 comprises a head 108 and an elongate member 110. The rear cap 104 and the plunger 106 are connected to each other such that before firing, relative axial movement between them is resisted or prevented. The connection between the rear cap 104 and the plunger 106 is releasable such that after activation of the auto-injector 100, relative axial movement between them is permitted. The nature of the releasable connection is discussed in more detail below.

The firing assembly 102 also comprises a biasing member 112 for driving the plunger 106 axially forwards and into a barrel of a syringe (shown in FIG. 2) retained within the auto-injector 100. In one example the biasing member 112 is a drive spring (e.g. a compression spring) and will be referred to as such throughout, although this should not be construed as limiting and the skilled person will appreciate that other means may be used to drive the plunger forwards.

Figure 2:
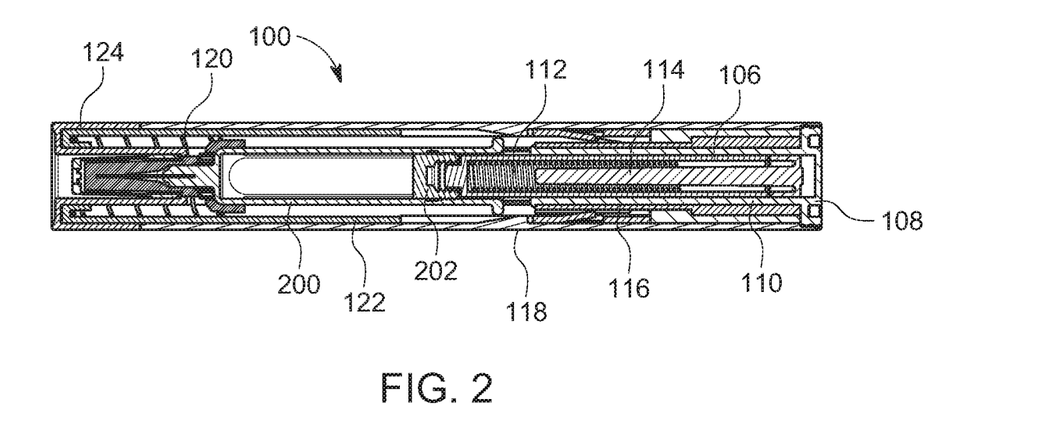
FIG. 2 is a section through an auto-injector with a syringe fitted therein.

In the example of FIG. 1, the plunger 106 is telescopically received within the elongate member 110 of the rear cap 104. The drive spring 112 is positioned between the rear cap 104 and the plunger 106 such that they are biased in opposite axial directions relative to each other. This is best shown in FIG. 2, which is a section through an auto-injector 100 in an assembled state before activation and with a syringe 200 retained therein. The plunger 106 is received within the elongate member 110. The plunger 106 is a hollow tube with an open end at the rear and the drive spring 112 is received within the plunger 106. A first end of the drive spring 112 abuts a forward end of the plunger 106 and a second end of the drive spring 112 is fixed with respect to the rear cap at least during delivery of a medicament from the syringe. In the example of FIG. 2, the drive spring 112 is coupled to an end of dose indicator 114, which in turn is coupled to the rear cap 104. The end of dose indicator provides a reaction component against which the drive spring 112 reacts. Expansion of the drive spring 112 drives the plunger 106 forwards into the barrel of the syringe 200.

In FIG. 2, a forward end of the plunger 106 is shown abutting a bung 202. This will not always be the case, as discussed above.

The auto-injector 100 also comprises a clutch 116, which is positioned around the elongate member 110. Before activation of the auto-injector 100, the clutch 116 is rotationally coupled to the plunger 106 and to the end of dose indicator 114. Rotation of the clutch 116 therefore causes rotation of the plunger 106 and the end of dose indicator 114. As explained below, on activation of the auto-injector 100, the clutch 116 rotates, thereby rotating the plunger 106 relative to the rear cap 104 to release the connection therebetween. Operation of the clutch 116, and of the end of dose indicator 114, is explained in more detail below.

The auto-injector 100 also comprises a main body 118, which houses the firing mechanism 102, the syringe 200 and other features necessary for operation of the auto-injector 100. The main body 118 may comprise a plurality of separate parts. The main body 118 comprises a syringe locator, which in exemplary arrangements comprises one or more features for receiving and optionally retaining a syringe in position within the main body 118.

The auto-injector also comprises a lockout spring 120 and lockout shroud 122, wherein the lockout spring 120 is configured on release thereof to displace the lockout shroud 122 axially forwards to cover a needle of the syringe. A cap 124 also forms part of the auto-injector and covers a needle or forward end of the auto-injector prior to use.

Figures 3A, 3B:
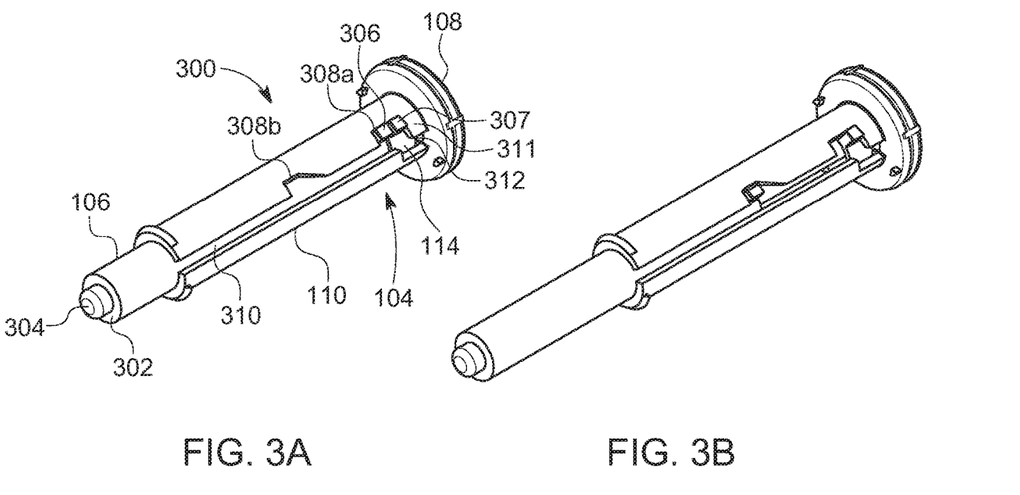
FIGS. 3a and 3b show perspective views of exemplary firing mechanism assemblies.

FIGS. 3a and 3b show perspective views of an assembly 300 for a firing mechanism. The assembly 300 comprises the rear cap 104 and the plunger 106. The plunger 106 is telescopically received within the elongate member 110. The assembly 300 also comprises a plunger driver to drive the plunger 106 axially forwards, which in the exemplary arrangements disclosed herein comprises a compression spring although the skilled person will understand that other arrangement are possible.

The exemplary plunger 106 comprises a cylindrical tube that is open at a rear end and closed at a forward end. The forward end of the plunger 106 comprises a shoulder 302 and a projection 304 configured to engage a bung 202 in a syringe barrel. The plunger 106 also comprises a lug 306 configured to engage with any of a plurality of recesses 308a, 308b in the elongate member 110. In the exemplary arrangements of FIGS. 3a and 3b the lug 306 extends radially from on outer surface of the plunger 106.

The elongate member 110 comprises an axial channel 310. The plurality of recesses 308a, 308b are formed in a sidewall of the channel 310. That is, the plurality of recesses 308a, 308b extend circumferentially (or transverse to the axial channel) around the outer wall of the elongate member 110. It is noted that while only two recesses 308a, 308b are shown in FIGS. 3a and 3b, more recesses (e.g. three—as shown in FIG. 4—or four) may be provided in the elongate member 110. The recess 308b comprises an angled rear surface and a front surface that is perpendicular to an axial direction (or longitudinal axis) of the auto-injector 100. The recesses 308a, 308b are configured to receive the lug 306 of the plunger 106. FIG. 3a shows the lug 306 received in a rearward recess 308a and FIG. 3b shows the lug 306 received in a forward recess 308b.

The channel 310 and the recesses 308a, 308b are configured such that rotation of the plunger 106 relative to the elongate member 110 in a first direction moves the lug 306 into the recesses 308a, 308b and rotation in a second, opposite direction moves the lug 306 out of the recesses 308a, 308b.

The plunger 106 and the rear cap 104, in particular the elongate member 110, define an axial length of the assembly 300. The axial length of the assembly 300 determines a start position of the forward end of the plunger 106 before release of the connection of the plunger 106 the elongate member 110. This can be seen in FIGS. 3a and 3b, which show the plunger 106 releasably connected to the elongate member 110 at different points, thereby controlling the overall axial length of the assembly 300.

During assembly, the plunger 106 is connected to the elongate member 110 at any of a plurality of positions on the elongate member 110 and/or the plunger 106 to alter a combined axial length of the plunger 106 and the elongate member 110. The connection may be made directly or indirectly through a plunger carrier, as explained below. In the example of FIGS. 3a and 3b, a direct connection is made. The plunger 106 may be received within the elongate member 110 such that the lug 306 is in the channel 310. The plunger 106 may then be displaced relative to the elongate member 110 until the lug 306 is aligned with one of the recesses 308a, 308b. The plunger 106 may then be rotated such that the lug is received within the one of the recesses 308a, 308b with which it was aligned. The force provided by the drive spring 112 retains the lug 306 within the recess 308a, 308b against the forward surface thereof. The combined axial length of the assembly (i.e. of the rear cap 104 and the plunger 106) is increased in FIG. 3b when compared to FIG. 3a, in which the lug 306 is received within the rearward recess 308a.

FIGS. 3a and 3b further illustrate a rear end of the end of dose indicator 114 which includes a lug 307 projecting radially outward. In the configuration of FIG. 3(a) the lug 307 engages with the recess 308a formed in the sidewall of the channel 310, immediately behind the lug 306 of the plunger 106. In the configuration of FIG. 3(b) the lug 307 also engages with the recess 308a whilst the lug 306 of the plunger 106 engages with the lower recess 308b as described above.

Figure 4A:
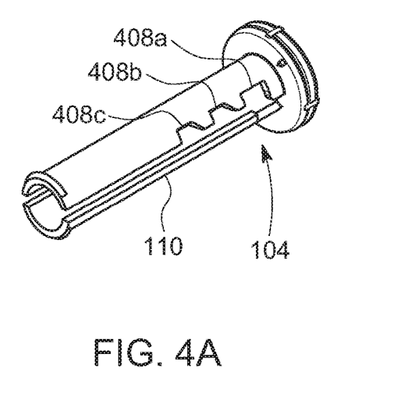
FIGS. 4a and 4b show perspective views of exemplary rear caps.
Figure 4B:
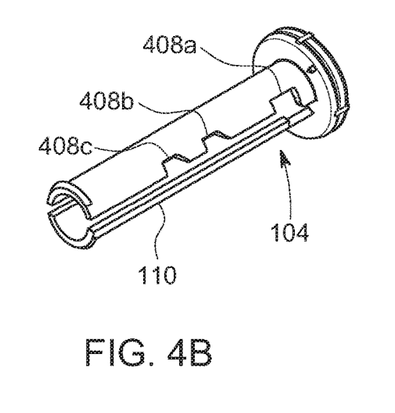

FIGS. 4a and 4b show alternative rear caps 104 having three recesses 408a, 408b, 408c. It will be appreciated that other numbers of recesses may be used. In addition, the recesses 408a, 408b, 408c may be positioned at any point on the elongate member 110. In the exemplary arrangement of FIG. 4b, the recesses 408b and 408c have been displaced forwards with respect to those in FIG. 4a. It will be appreciated that the lug 307 of the end of dose indicator 114 is always retained, prior to activation, within the rearmost recess 408a, whilst the position of the lug 306 of the plunger 106 may be retained within that same recess or one of the lower recesses.

Figure 5:
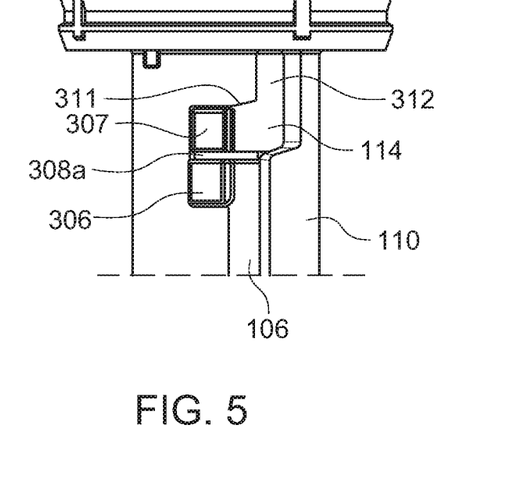
FIG. 5 illustrates a state of internal parts of the device prior to device activation.

As best seen in the detail of FIG. 5, the recess 308a (or 408a with reference to FIGS. 4a and 4b) presents a rear stop surface 311 extending in a generally circumferential direction. The circumferential extent of the stop surface 311 is such that combined rotation of the plunger 106 and end of dose indicator 114 to a position such that the plunger lug 306 is located within the channel 310 results in the continued blocking of the lug 307 (preventing rearward movement of the end of dose indicator 114). However, further rotation of the end of dose indicator 114, as will be described below, takes the lug 307 past the end of the stop surface 311 and aligns it with an effective upper extension 312 of the channel 310.

During assembly of the auto-injector, the assembly comprising the plunger, the end of dose indicator and the rear cap is set using any of the methods and apparatus described herein. The plunger and end of dose indicator are connected to the elongate member of the rear cap. The connection is releasable in that, upon activation of the auto-injector, the connection is released to allow relative axial movement of the plunger and the rear cap. Also, the connection may be made at any of a plurality of positions on the elongate member or the plunger. That is, one or both of the elongate member and the plunger may be configured to have a plurality of locations at which the connection may be made.

Accordingly, the combined axial length of the plunger and the rear cap is set to the desired length based on a fill volume (or bung position) of a syringe that the auto-injector is intended for use with. In so doing, the gap between the bung of the syringe, which sits at a position in the barrel that is dependent on the fill volume, is controlled. That is, if the combined axial length of the plunger and the rear cap is extended then the auto-injector may be used for syringes having a smaller fill volume, or otherwise having a bung that is initially positioned further forwards within the barrel, e.g. if the barrel is of a greater diameter but the fill volume remains the same. The start position of a forward end of the plunger is adjusted during assembly.

Once assembled, the user has no control over the combined length of the rear cap and the plunger. Operation of the auto-injector 100 is described below using the reference numerals of the exemplary arrangement shown in FIGS. 1 to 3, with reference to the further figures as appropriate.

In use, a user removes the cap 124 of the auto-injector 100, which in turn removes a rigid needle shield covering the needle. Removal of the cap exposes the lockout shroud 122, which protrudes from a forward end of the body 118.

The user places a forward end of the lockout shroud 122 against an injection site and pushes the auto-injector 100 downwards onto the injection site. This action pushes the lockout shroud 122 rearwards within the auto-injector 100. The lockout shroud interacts with the clutch 116 to rotate it. This may be done by forcing a surface (or pip) of the lockout shroud 122 against an angled surface on the clutch 116, which translates the rearward motion of the lockout shroud 122 into rotational motion of the clutch 116.

In some arrangements, an insertion spring may be activated by the action of pushing the auto-injector 100 onto the injection site and the insertion spring may drive the syringe forwards within the device to insert the needle into the injection site. In other arrangements, the force applied by the drive spring 112 acting against the bung may be used to insert the needle. In yet further arrangements, the syringe may be fixed in relation to the injection device 100 and the force applied by the user when pushing the auto-injector 100 onto the injection site may insert the needle into the injection site.

As the clutch 116 is rotationally coupled to the plunger 106 and to the end of dose indicator 114, rotation of the clutch 116 causes rotation of the plunger 106 and the end of dose indicator 114. In some arrangements, the clutch 116 may have an internal track located on an internal wall thereof and that receives a lug of the plunger 106 and a lug of the end of dose indicator 114. These lugs may be the same as the lugs 306, 307 described with reference to FIGS. 3a and 3b. Rotation of the plunger 106 with respect to the rear cap 104 releases the connection between the rear cap 104 and the plunger 106, allowing the plunger 106 to be driven forwards under force of the drive spring 112. In the examples of FIGS. 1-4, this is provided by rotating the lug 306 of the plunger rod 106 out of whichever recess 308a, 308b, 408a-408c the lug 306 was positioned in and into the axial channel 310. The lug 306 is thereby allowed to travel forwards within the channel 310.

Figure 6:
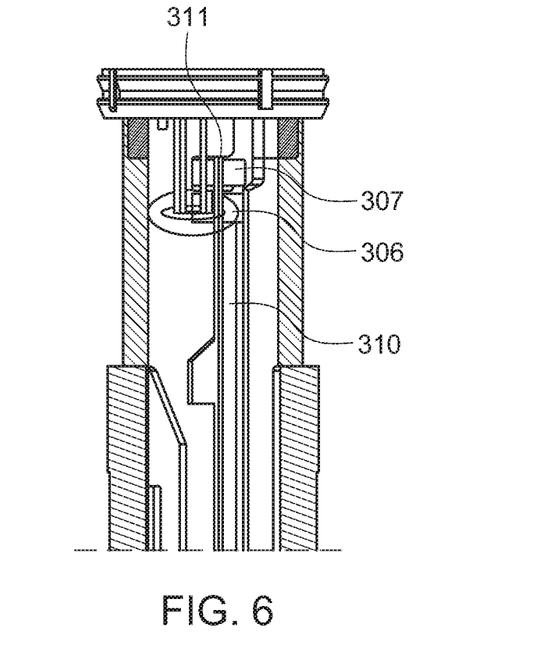
FIG. 6 illustrates a state of internal parts of the device at an activation state and before forward movement of a device plunger commences.

FIG. 6 illustrates the state of the device immediately following rotation of the lug 306 out of the recess 308a and into the channel 310. In this state, the lug 307 of the end of dose indicator 314 has been rotated to the same extent.

The drive spring 112 then acts against the plunger 106 and the rear cap 104 via the end of dose indicator 114 which is prevented from moving rearwards by the stop surface 311. Because the rear cap 104 is fixed within the auto-injector 100, the force delivered by the drive spring 112 acts to drive the plunger 106 into the barrel of the syringe. Because the gap between the forward end of the plunger 106 and the bung 202 has been controlled during assembly, the plunger 106 does not accelerate above a safe velocity that would risk damage to the syringe 200 or harm or discomfort to the subject of the injection.

Figure 7A:
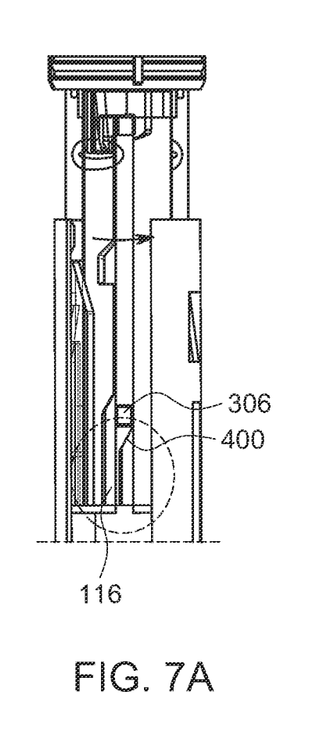
FIGS. 7a to 7c illustrate partial cross-section various states of the device during forward movement of the plunger.
Figure 7B:
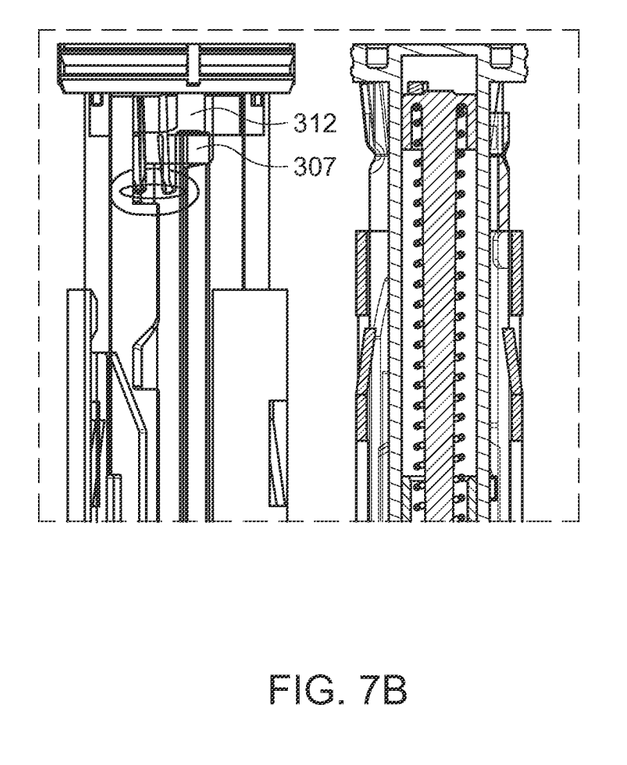
Figure 7C:
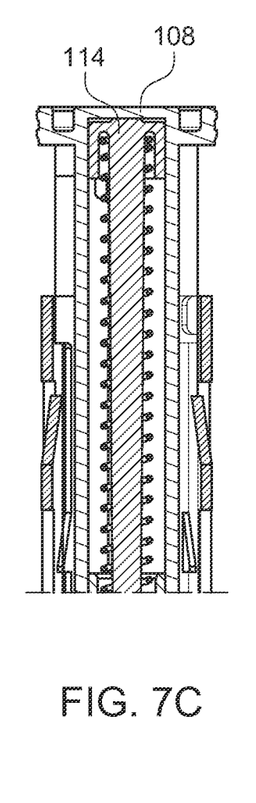

FIGS. 7a to 7c illustrate subsequent series of steps that result in an end of dose indication being provided to a user.

FIG. 7a The plunger 106 has been driven forward to a position at which the lug 306 of the plunger meets a rotation ramp 400 provided on an inner surface of the clutch 116. As the lug 306 remains confined within the channel 310 of the elongate member 110, and therefore cannot rotate relative to the elongate member 110, the lug 306 causes the clutch 116 to rotate (counter-clockwise when viewed from the rear end of the device). Rotation of the clutch 116 by the lug 306 in turn rotates the end of dose indicator 114 (again in a counter-clockwise direction) due to engagement of the clutch with the lug 307.

FIG. 7b The lug 307 is moved across the stop surface 311 (FIG. 5) until the lug is free to move rearward into the channel extension 312. This state is shown in the left view of FIG. 7b. The right view of FIG. 7b is a full cross-sectional view of the rear end of the device in this state. Part of the stop surface 311 may be slightly angled to encourage rotation of the lug 307 across the stop surface.

FIG. 7c As the lug 307 is now free to move rearwardly along the channel extension 312, the end of dose indicator 114 is forced rearwards by the force exerted by the drive spring 112 until an end of the end of dose indicator strikes an inner surface of the head 108 of the rear cap. This impact results in an audible sound or click.

Referring again to FIG. 7a, it will be apparent that the final rotation of the clutch which results in rotation and release of the end of dose indicator occurs slightly ahead of the plunger bottoming out relative to the syringe. The audible click therefore occurs shortly in time ahead of the actual end of dose. However, given the auditory processing delay of the user, the click is perceived to occur at the actual end of dose point or slightly thereafter.

It will be appreciated by the person of skill in the art that various modifications may be made to the above described embodiments without departing from the scope of the present invention.

The invention claimed is:

1. An injection device comprising:
a body for receiving a syringe;
a firing mechanism comprising a reaction component, a plunger configured to be axially displaced in a forward direction relative to the reaction component, and a drive spring located between the reaction component and the plunger for driving the plunger forwards upon activation of the injection device, wherein said reaction component provides a reaction surface for the drive spring; and
a locking mechanism for locking the reaction component in a first axial position within the body, the locking mechanism being configured to release the reaction component upon a predefined forward movement of the plunger thereby allowing the reaction component to be driven in a rearward axial direction by the drive spring until the reaction component impacts against said body or a component secured to the body to thereby emit an audible indication of an end of dose,
said locking mechanism comprising a stop feature having a fixed axial position relative to said body, and a feature for causing a rotation of the reaction component within the body, substantially upon said predefined forward movement of the plunger, to move the reaction component out of a blocking engagement with said stop feature and thereby allow rearward movement of the reaction component.

2. The injection device according to claim 1 comprising a rear cap fixed to a rear end of said body, the rear cap providing said component against which the reaction component impacts to emit an audible indication of an end of dose.

3. The injection device according to claim 2, wherein said feature for causing a rotation of the reaction component within the body comprises a clutch having a substantially fixed axial position, the clutch being rotatable within the body by axial movement of the plunger towards the end of a delivery stroke to thereby cause said rotation of the reaction component.

4. The injection device according to claim 3, wherein said clutch is a substantially cylindrical component within which said plunger, said drive spring and said reaction component and are coaxially accommodated.

5. The injection device according to claim 4, wherein said reaction component comprises an elongate rod extending through the drive spring and an enlarged head at a rearward end of the rod, wherein the head provides said reaction surface and a surface that impacts the rear cap.

6. The injection device according to claim 4, further comprising a lockout shroud extending from a forward end of said body and being configured to cause activation of the device when pressed into the body.

7. The injection device according to claim 3, wherein said reaction component comprises an elongate rod extending through the drive spring and an enlarged head at a rearward end of the rod, wherein the head provides said reaction surface and a surface that impacts the rear cap.

8. The injection device according to claim 7, wherein said rear cap comprises a skirt extending into the body from said rear end of the body and which defines a substantially longitudinally extending channel, said plunger and said reaction component being received within the skirt and being provided respectively with a plunger lug and a reaction component lug, said lugs being receivable within said channel to guide axial movement of the plunger and the reaction component.

9. The injection device according to claim 8, said skirt further defining a recess extending from said channel in a substantially circumferential direction and within which said lugs are located prior to device activation, said clutch being rotatable within the body upon activation to move the lugs into the channel.

10. The injection device according to claim 9 and comprising a circumferential deviation of said channel rearwards of said recess in order to provide said stop feature, whereby the reaction component is prevented from moving rearward upon said activation but is permitted to move rearwards at the end of the plunger stroke.

11. The injection device according to claim 9 and comprising a lockout shroud extending from a forward end of said body and being configured to cause activation of the device when pressed into the body.

12. The injection device according to claim 11, wherein said lockout shroud causes activation of the device by rotating said clutch as the lockout shroud is pressed into the body to thereby move the lugs of the plunger and the reaction component out of said recess and into the channel.

13. The injection device according to claim 7, further comprising a lockout shroud extending from a forward end of said body and being configured to cause activation of the device when pressed into the body.

14. The injection device according to claim 3, further comprising a lockout shroud extending from a forward end of said body and being configured to cause activation of the device when pressed into the body.

15. The injection device according to claim 2, further comprising a lockout shroud extending from a forward end of said body and being configured to cause activation of the device when pressed into the body.

16. The injection device according to claim 1, wherein said drive spring is a compression spring configured to expand upon activation of the device.

17. The injection device according to claim 1, further comprising a rear cap fixed to a rear end of said body, the rear cap providing said component against which the reaction component impacts to emit an audible indication of an end of dose.

18. The injection device according to claim 1, further comprising a lockout shroud extending from a forward end of said body and being configured to cause activation of the device when pressed into the body.

19. The injection device according to claim 1, further comprising a lockout shroud extending from a forward end of said body and being configured to cause activation of the device when pressed into the body.

* * * * *